United States Patent [19]

Schwanbom et al.

[11] Patent Number: 4,519,388
[45] Date of Patent: May 28, 1985

[54] RESPIRATOR APPARATUS AND METHOD OF OPERATION THEREOF

[75] Inventors: Erik Schwanbom, Lübeck; Horst Frankenberger, Bad Schwartau, both of Fed. Rep. of Germany; Marcel Baum, Vienna, Austria

[73] Assignee: Drägerwerk A.G., Fed. Rep. of Germany

[21] Appl. No.: 378,386

[22] Filed: May 14, 1982

[30] Foreign Application Priority Data

May 19, 1981 [DE] Fed. Rep. of Germany ....... 3119814

[51] Int. Cl.³ ............................................. A61M 16/00
[52] U.S. Cl. ........................... 128/204.25; 128/207.15
[58] Field of Search ................... 128/207.15, 207.14, 128/204.25, 205.24, 204.19, 204.24, 205.19, 205.13, 204.26, 204.27, 204.21

[56] References Cited

U.S. PATENT DOCUMENTS

| | | | |
|---|---|---|---|
| 3,079,915 | 3/1963 | Stanton | 128/204.25 |
| 3,191,596 | 6/1965 | Bird et al. | 128/204.25 |
| 3,485,243 | 12/1969 | Bird et al. | 128/204.25 |
| 3,628,532 | 12/1971 | Magrath | 128/205.24 |
| 3,993,059 | 11/1976 | Sjöstrand | 128/205.13 |
| 4,265,237 | 5/1981 | Schwanbom et al. | 128/204.24 |
| 4,270,530 | 6/1981 | Baum et al. | 128/204.25 |
| 4,351,329 | 9/1982 | Ellestad et al. | 128/204.21 |

FOREIGN PATENT DOCUMENTS

| | | | |
|---|---|---|---|
| 1477987 | 9/1976 | United Kingdom | 128/204.25 |
| 2024021 | 1/1980 | United Kingdom | 128/204.25 |
| 2033759 | 5/1980 | United Kingdom | 128/204.25 |
| 2063686 | 6/1980 | United Kingdom | 128/204.25 |

Primary Examiner—Henry J. Recla
Assistant Examiner—Karin M. Reichle
Attorney, Agent, or Firm—McGlew and Tuttle

[57] ABSTRACT

A respirator device particularly for use in association with a tube insertable into a person's trachea comprises a trachea tube having an inflatable cuff which seals the tube with the person's trachea. A line for ventilating gas extends into the tube and terminates in a jet nozzle directed to the trachea. The opposite end of the tube is provided with a connection to atmosphere which also makes it possible to provide a controlled vacuum pressure at this end particularly in the expiration phase. Control is effected between the ventilating gas and the vacuum for regulating the respiration. With the inventive method the vacuum is provided at the outer end of the trachea tube particularly during respiration and it is effected by directing a vacuum pressure gas supply connection through a Venturi connection to the tube which produces the vacuum in the tube and communicates the tube to atmosphere. This gas connection is controlled along with a ventilating pressure gas connection to provide the desired respiration.

3 Claims, 1 Drawing Figure

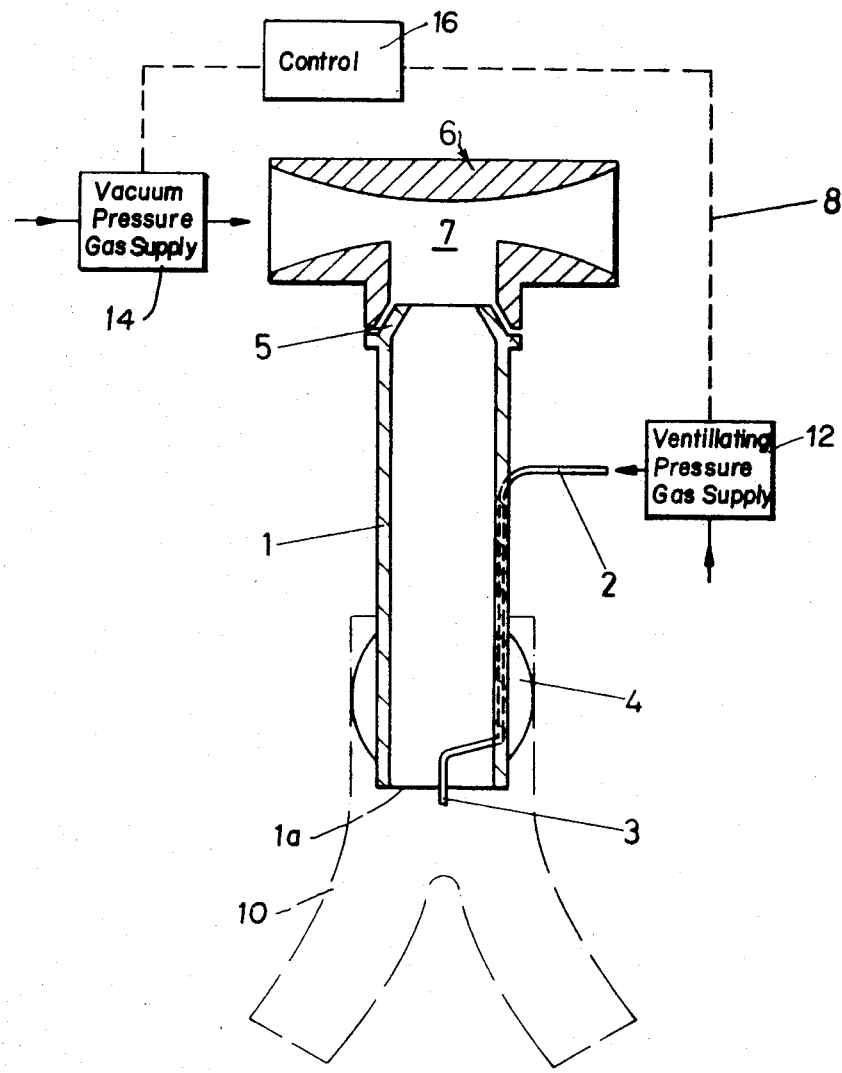

RESPIRATOR APPARATUS AND METHOD OF OPERATION THEREOF

FIELD AND BACKGROUND OF THE INVENTION

This invention relates in general to a respirator device particularly for use in association with a person's trachea into which a tube is inserted and which includes means for supplying ventilating gas in a jet stream through the tube and for connecting the opposite end of the tube to the atmosphere and providing a controlled vacuum therein.

The invention concerns a respirator with a ventilating gas source controlled over a control device which feeds at least one jet nozzle arranged in the range of the distal end of a tracheal tube and within the inspiration phase with gas high-pressure pulses, whose sequential frequency is above the natural ventilation frequency, particularly above 300/min. and which includes a control device which switches at the end of the inspiration phase to the expiration phase and where a given pressure value deviating from the ambient atmosphere can be set at the proximal end of the tracheal tube.

An alternating positive-negative pressure ventilation (APV) can be effected with various known respirators. Depending on the selection of the positive and negative ventilation pressures and of the phase time ratio, the mean ventilation pressure can be kept in the positive or negative range or on the zero line.

An apparatus for alternating pressure ventilation is described in German patent No. 916,727. By means of an injector fed with ventilating gas, the air is exhausted from the lungs until a corresponding vacuum has been attained. This vacuum effects the switching of the injector action over control valves in such a way that the gas now arriving from the injector is forced into the lungs until a certain pressure value has been attained. The switching between the respiration phase is effected by means of a diaphragm controlled valve whose motion drive is based on the pressure difference between a space in communication with the lungs and the ambient atmosphere.

From German patent application No. P 29 47 659.3 is known a respirator with a ventilating gas source controlled by patient values over a control device, which can be operated with a tracheal tube or an insufflation catheter with jet nozzle, where the ventilating gas source generates in HFJV-operation (high-frequency jet ventilation) gas high-pressure pulses which form respiration pulse series and leave between these respiration pulse series intervals for expiration. A closing element permits the setting of a given pressure value deviating from the ambient atmosphere at the proximal end of the tracheal tube.

SUMMARY OF THE INVENTION

The invention improves the effectiveness during the expiration phase in a respirator for HFJV, and particularly of permitting a complete exhaust of the generated $CO_2$, whereby the respirator interferes as little as possible with spontaneous respiration or sudden coughing spells etc. For the solution of this problem the tracheal tube is connected at least in the expiration phase to an apparatus for generating a vacuum, which establishes in both respiration phases a connection of the proximal tube end with the ambient atmosphere.

The advantage of such a respirator is that it permits free ventilation at any time, that is, in the inspiration and expiration phase, and that coughing spells can be shunted, so that barotraumas can be prevented. In addition, by applying a vacuum in the expiration phase, a substantial improvement of HFJV can be achieved in such a way that the $CO_2$, which is increasingly produced at a high metabolic rate, can be better exhausted by increasing the pressure gradient between the alveolar space of the lungs and the distal tube end.

Though the tracheal tube is to be connected at least in the expiration phase to the apparatus for generating a vacuum, it may be advisable to maintain this connection in the inspiration phase and in the expiration phase. The effectiveness of a high-frequency ventilation method is determined primarily by the possibility of eliminating the carbon dioxide from the lungs. In the terminal bronchial sections, the elimination of carbon dioxide is effected primarily by diffusion and depends thus on the length of the diffusion paths.

By applying a negative pressure valve in the inspiration and expiration phase it is possible to obtain such an insufflation state in the lungs, where the diffusion paths are shortened in the desired manner.

The size of the vacuum generated with the apparatus is preferably adjustable. Of advantage seems also to be a design where the control device controls the size of the vacuum according to the amount of ventilating gas supplied by the ventilating gas source in the form of gas high-pressure pulses in such a way that a higher vacuum corresponds to a larger amount of ventilating gas. In an expedient further development, the apparatus for generating a vacuum can be so designed that it generates vacuum pulses with sequential frequencies from 10/min to 1000/min. The duration of these vacuum pulses can be between 1 ms and 250 ms. the vacuum being preferably in a range between 2 and 25 mbar.

It seems advisable to synchronize the vacuum pulses with the gas high pressure pulses by a control device in such a way that a gas high pressure pulse or a series of such pulses is followed by at least one vacuum pulse or likewise by a series of vacuum pulses.

An advantageous apparatus for generating a vacuum can likewise be so designed that a Venturi tube, fed from a servo-gas source, is provided at the proximal end of the tracheal tube whose flow determines the vacuum in the tracheal tube. Preferably the Venturi tube is arranged in an extension piece that can be attached on the tracheal tube. The cross section of the exhaust connection and the flow cross section of the Venturi tube should preferably correspond at least approximately to the free cross section of the tracheal tube.

Instead of a Venturi tube can also be used other apparatus for generating a vacuum, e.g. injector type nozzle arrangements, which are likewise fed from a servo-gas source and which permit free ventilation.

The inventive device is particularly useful for connecting a person's trachea to a respirator and advantageously comprises a trachea tube which is insertable into the person's trachea and which has an inflatable cuff associated therewith for sealing the tube with the space between the tube and the trachea. The line for ventilating gas extenqs into the tube and terminates in a jet nozzle directed out of the tube and into the person's trachea. The device also includes a connection at the outer end of the tube to atmosphere and to means for producing a control vacuum which in the preferred embodiment comprises a Venturi tube through which a controlled pressure gas is directed.

In accordance with the method of the invention, the respirator connection for inspiration and expiration to a person's trachea includes a tube which is insertable into the trachea and has an opposite open end and the method comprises directing a ventilating gas into the trachea through the tube in the form of a jet stream and particularly during the expiration providing a vacuum adjacent the open end.

A further object of the invention is to provide a device for use in a person's trachea for respiration purposes which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE of the drawing is a schematic view of a Person's trachea having a tracheal tube and respirator connected thereto constructed in accordance with the invention.

DESCRIPTION OF THE PREFERRED EMBODIMENT

Referring to the drawing, in particular the invention embodied therein comprises a respirator for use in supplying a respiration gas to a person's trachea 10 using a tracheal tube 1 which is inserted into the trachea, for example after an incision is made to connect thereto. The tracheal tube 1 includes an inner end 1a disposed within the trachea 10 sealed to the wall of the trachea by an inflatable cuff 4 which is associated with the tracheal tube. A ventilating or respirating gas is supplied under pressure from a ventilating pressure gas supply 12 which is directed through a supply line 2 extending through a wall of the tube 1 and then terminates in a jet nozzle 3 extending out of the inner end 1a of the tube into the person's trachea 10.

In accordance with a feature of the invention means are provided at the opposite open end or conical end portion 5 of the tracheal tube 1 which are generally designated 6 and which connect the tube to atmosphere and provide means for creating a selected vacuum in a Venturi tube neck portion 7 which communicates with the outer end of the tube 1. In the embodiment illustrated the vacuum providing an atmosphere connecting part 6 in the form of an extension piece having one end connected to a servo-gas or pressure-gas supply 14. A control 16 is located in a synchronizing line between the pressure gas supply 14 and the ventilating pressure gas supply 12 in order to provide a regulation between these supplies to their associated extension piece 6 and supply line 2 respectively.

The tracheal tube 1 has the supply line 2 for ventilating gas (jet gas) molded into its wall portion, which opens into a single jet nozzle 3 or into separate jet nozzles (not shown) for both lungs. For sealing from the bronchial trunk, the inflatable cuff 4 is provided on the outer surface of tracheal tube 1.

On the conical proximal end portion 5 of the tracheal tube 1 is attached the extension piece 6 whose flow surface correspond approximately to the free cross section of the tracheal tube 1. Venturi tube neck 7 is formed by constriction in the recess extending perpendicularly to tracheal tube 1.

The controlled generation of a vacuum is effected in this way that a pressure gas is supplied over the servo-gas source in a controlled manner to the Venturi throat 7 so that a corresponding vacuum appears in the interior of tracheal tube 1.

In the inspiration phase the respirator is supplied in the form of gas high-pressure pulses by the jet gas source 12 over supply line 2 to jet nozzle 3. The pulses are at a frequency of above 300 cycles per minute. The control device in the jet gas source 12 and the control device in the servo-gas source 14 are connected over a synchronizing line 8 to the balancing control 16. This has the effect that the size of the vacuum can be adapted to the amount of ventilating gas, and that a group of gas high-pressure pulses is followed by a corresponding vacuum segment of the expiration phase or a series of vacuum pulses in synchronism.

While a specific embodiment of the invention has been shown and described in detail to illustrate the application of the principles of the invention, it will be understood that the invention may be embodied otherwise without departing from such principles.

What is claimed is:

1. A respirator device for use in a patient's trachea comprising:

a tracheal tube (1) having one open end (1a) adapted for insertion into a person's trachea, and an opposite open end (5);

a line (2) for ventilating gas extending into said tracheal tube and terminating in a jet nozzle (3) directed out of said tube one open end (1a) into the person's trachea;

ventilating gas supply means (12) connected to said jet nozzle via said line (2) for supplying ventilating gas in gas jet pulses having a frequency above 300 cycles per minute during an inspiration phase of said respirator device;

an extension piece (6) defining a through passage therethrough having an input end, an output end and an intermediate necked down portion (7), said output end communicating with the atmosphere, said opposite open end of said tracheal tube connected to said extension piece between the input and output ends and substantially perpendicular thereto and said extension piece defining a connecting passageway extending between the interior of said trachea tube at said opposite open end (5) and said necked down portion (7) of said extension piece through passage, said through passage shaped so that when pressurized gas is applied to said input end a vacuum appears in the interior of said opposite open end (5) of said trachea tube (1);

vacuum pressure gas supply means connected to said extension piece and communicating with said input end of said through passage for supplying gas pulses for producing vacuum pulses in the interior of said opposite open end of said tracheal tube (5); and control means connected to said vacuum pressure gas supply means and to said ventilating gas pressure means for synchronizing vacuum pulses with jet gas pulses through said jet nozzle in such a way that a jet gas pulse or a series of jet gas pulses is followed by a vacuum pulse, and for controlling said vacuum pressure gas supply means for producing vacuum pulses with frequencies ranging from 10 to 1,000 cycles per minute.

2. A respirator device according to claim 1, wherein said through passage of said extension piece defines a venturi passage with said necked down portion having a smaller diameter than a diameter of said input and output ends of said through passage, said connecting passageway in said extension piece communicating said necked down portion with said opposite open end of said trachea tube having a cross section substantially equal to the cross section of the interior of said opposite open end of said trachea tube.

3. A respirator device according to claim 2, wherein said control means controls said vacuum pulses and said jet gas pulses so that the vacuum produced by said vacuum pulses corresponds proportionately to the amount of ventilating gas supplied in gas jet pulses.

* * * * *